(12) United States Patent
Obermann et al.

(10) Patent No.: US 8,093,015 B2
(45) Date of Patent: Jan. 10, 2012

(54) METHOD FOR DETERMINING THE VIABILITY OF CELLS IN CELL CULTURES

(75) Inventors: Stefan Obermann, Adelebsen (DE);
Reinhard Baumfalk, Göttingen (DE);
Oscar-Werner Reif, Hannover (DE);
Florian Wurm, Belmont-sur-Lausanne (CH); Maria de Jesus, Chavannes (CH);
Matthieu Stettler, Lausanne (CH);
Martin Jordan, Ecublens (CH)

(73) Assignee: Sartorius Stedim Biotech GmbH (DE)

( * ) Notice: Subject to any disclaimer, the term of this patent is extended or adjusted under 35 U.S.C. 154(b) by 372 days.

(21) Appl. No.: 12/227,186

(22) PCT Filed: Apr. 24, 2007

(86) PCT No.: PCT/EP2007/003568
§ 371 (c)(1), (2), (4) Date: Nov. 7, 2008

(87) PCT Pub. No.: WO2007/131596
PCT Pub. Date: Nov. 22, 2007

(65) Prior Publication Data
US 2009/0263848 A1   Oct. 22, 2009

(30) Foreign Application Priority Data
May 15, 2006  (DE) .......................... 10 2006 022 877

(51) Int. Cl.
*C12Q 1/02*   (2006.01)
*G01N 1/18*   (2006.01)
(52) U.S. Cl. ........................................ 435/29; 436/177
(58) Field of Classification Search ........................ None
See application file for complete search history.

(56) References Cited

FOREIGN PATENT DOCUMENTS

| DE | 103 29 539 A1 | 1/2005 |
|---|---|---|
| DE | 103 61 073 A1 | 7/2005 |
| EP | 1 293 205 A1 | 3/2003 |
| WO | WO 02/08454 A2 | 1/2002 |
| WO | WO 2005/063119 A1 | 7/2005 |
| WO | WO 2005/087253 A2 | 9/2005 |

OTHER PUBLICATIONS

Schoenherr et al., "A Comparison of Different Methods to Determine the End of Exponential Growth in CHO Cell Cultures for Optimization of Scale-Up", *Biotechnol. Prog.* 2000, 16, 815-821.

Maceyka et al., "Aminoacylase 1 is a sphingosine kinase 1-interacting protein", *FEBS Letters* 568 (2004) 30-34.

Schreer et al., "Application of Alamar blue/5-carboxyfluorescein diacetate acetoxymethyl ester as a noninvasive cell viability assay in primary hepatocytes from rainbow trout", *Analytical Biochemistry* 344 (2005) 76-85.

Luecke, "Fast, reproducible and reliable determination of biomass in suspension cell cultures with VoluPac tubes", *Nature Methods*, Oct. 2006, v-vi.

Stettler et al., "New Disposable Tubes for Rapid and Precise Biomass Assessment for Suspension Cultures of Mammalian Cells", *Biotechnology and Bioengineering*, vol. 95, No. 6, Dec. 20, 2006, 1228-1233.

*Primary Examiner* — Rebecca Prouty
*Assistant Examiner* — Paul Martin
(74) *Attorney, Agent, or Firm* — Gerald E. Hespos; Michael J. Porco

(57) ABSTRACT

The invention relates to a method for determining the viability of cells in cell cultures, said method comprising the steps of: coloring the sample with a dye which can penetrate into individual cells depending on the viability of the latter, determining the proportions of cells which are colored to differing extents. The invention is distinguished by virtue of the fact that a cell suspension of the colored cells is centrifuged as a sample in a sample vessel (10) until the solid content present in the sample has settled as a compressed cell cake (13), and, in order to determine the proportions, the volumes of differently colored sections (131, 132, 133) of the compressed cell cake (13) are determined as a measure of the proportions of cells of different viability.

13 Claims, 2 Drawing Sheets

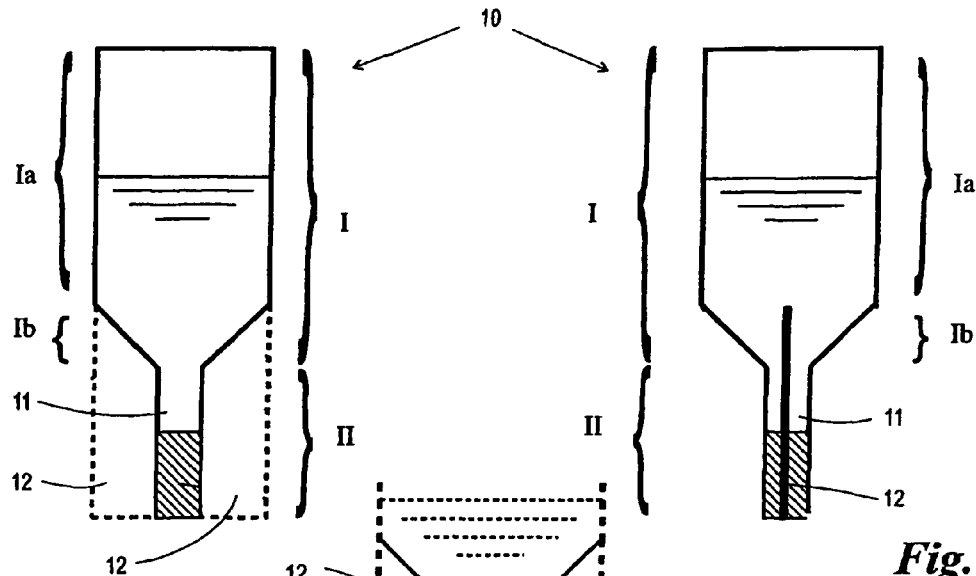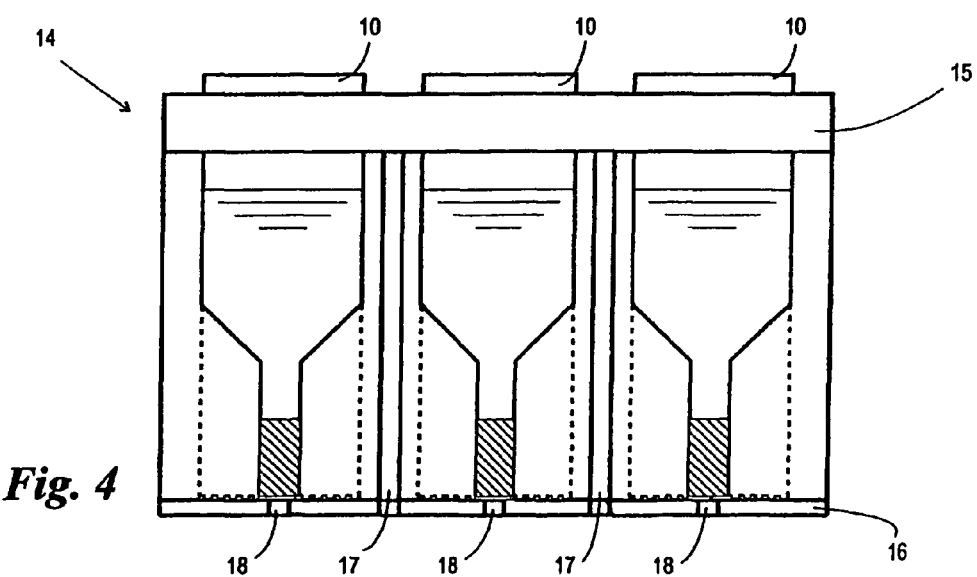

METHOD FOR DETERMINING THE VIABILITY OF CELLS IN CELL CULTURES

The invention relates to a method for determining the viability of cells in cell cultures, comprising the steps of:
staining the samples by a dye that can penetrate into individual cells as a function of their viability, and
determining the portions of cells stained with different intensities.

The so called trypan blue method is known for determining the viability, that is to say the "state of health" of cells in a cell culture. In this case, cells in suspension are stained with dye, which has the property of not being able to penetrate the cell membrane of intact cells. Damaged or dying cells, by contrast, permit the penetration of the dye and can thus be successfully stained. A strong diluted cell suspension is put into a so called Neubauer counting chamber in order to determine the proportions of intact and damaged cells. The dimensions of said chamber, correspond approximately to a conventional microscope slide, and it has a depression of defined size that is subdivided into a plurality of counting fields. Under the microscope, the cell numbers of stained, that is to say damaged, and non-stained, that is to say intact, cells can be counted up. The cell numbers in the individual counting fields are normally determined and averaged in order to reduce the statistical error. It is then possible to state the absolute quantities of the intact and damaged cells in the cell culture by back-calculating using the known values of the counting chamber volume and of the selected suspension dilution. This method is, firstly, very complicated, since it includes a multiplicity of manual steps. Secondly, its accuracy is also greatly limited. In particular, the cell numbers that can be counted up are very restricted, and this leads to a high statistical error. The method is therefore virtually incapable when the aim is not only to make a statement concerning the proportions of intact and damaged cells, in addition to make a differential statement concerning the distribution of the degree of damage of the cells. Such a statement would be possible in principle on the basis of a trypan blue staining, since the degree of staining of a cell can serve as a measure of its damage, particularly as a measure of the progress of its dying process. However, in order to validate such a distribution statistically, it is necessary to count up very large quantities of cells, and this would render the known method completely inefficient.

The so called PCV method is known from the field of diagnostics. PCV stands for "packed cell volume", and describes the proportion of solids in the form of a compressed cell cake in the total volume of a sample. The PCV value of the blood denoted as hematrocrit is also known. To determine this, a blood sample is centrifuged in a mostly cylindrical sample tube until the solids content of the blood has been deposited as a compressed cell cake at the tube bottom. The liquid content, which is also denoted as supernatant, floats on the cell cake. In order to determine the hematrocrit, the volume of a cell cake is determined and put into a percentage ratio with the total volume of the sample. There is a disadvantage in the determination of the PCV value in that it admits only a total fraction of solids in the sample and, in particular, permits no statement concerning the viability of the cells in this solids content.

It is the object of the present invention to improve the known method for determining viability of cells in such a way as to permit a more accurate determination of the viability in an efficient way.

This object is achieved in conjunction with the method of the subject invention for determining the viability of cells in cell cultures by virtue of the fact that a cell suspension of the stained cells is centrifuged as a sample in a sample vessel until the solids content present in the sample has been deposited as a compressed cell cake and in that in order to determine the proportions the volumes of differently stained sections of the compressed cell cake are determined as a measure of the proportions of cells of different viability.

This means that the stained cells are subjected to the technical steps of the PCV method, but that, otherwise than in the PCV method, not (only) is the total volume of the compressed cell cake determined, but the partial volumes of its differently stained sections are determined.

The volume determination is preferably undertaken by ascertaining the heights of the corresponding cell cake sections from which the corresponding volume can be ascertained given knowledge of the geometry of the sample vessel. Particularly in the case of the use of sample vessels of constant cross section in the region of the cell cake, the height distribution of the individual sections corresponds directly to the volume distribution.

The essential basis of the invention is the realization that the solids contents deriving from intact and damaged cells exhibit different densities, and so they can be separated by centrifuging. It has emerged surprisingly that not only is this valid for completely intact cells, on the one hand, and destroyed cells, that is to say cell fragments, on the other hand, but that stained cells in different stages of the dying process can also be distinguished with regard to the density, and can thus be separated by centrifuging.

In a particularly advantageous embodiment of the inventive method, this can be utilized in that in order to determine the distribution of cells of different degree of damage a staining profile is ascertained in the direction of the cell cake height of at least one section of the cell cake. As a rule, three distinguishable sections of the cell cake are found in the case of typical cell cultures. In a first area, in which dead cells and cell fragments are stored, a uniform, maximum staining is found. In another area, which reaches completely intact cells, virtually no staining is found. Extending therebetween as a rule is a transitional area that will exhibit different shadings in an ordered way from virtually minimum to virtually maximum staining. This area shows a staining profile or staining gradient in the direction of the cell cake height. A detailed determination of this staining profile represents the distribution of different damaged cells. Such a differentiated view is sensible thanks to the present invention since, by contrast with the viability determination methods of the prior art, a large number of cells contribute to the measurable staining signal such that said profile determination is also statistically valid.

Whereas in the case of the abovedescribed hematocrit measurement method the typical measured values fall in the range of 30-50%, the total solids values to be expected in the case of cell cultures are substantially lower, typically in the range of 1% or therebelow. This means that when the sample vessels customary for the hematocrit determination are used for the inventive method the height of the supernatant column is approximately one hundred times the height of the cell peak. This can easily lead to large readoff errors, which acts disadvantageously, particularly when, as discussed above, more detailed statements concerning the distribution of differently viable cells are to be made.

In the case of a particularly favorable embodiment of the inventive method, it is therefore provided that the sample vessel has a holding area and a measuring area which adjoins the latter and is designed as a capillary, and whose inside diameter is substantially smaller than the inside diameter of the holding area. Subsequently, a scale transformation is achieved such that a given volume corresponds to a very much larger height in the measurement area than in the holding area. The use of a capillary with a diameter in the range of 500 micrometers and a volume from one to ten microliters, in particular two to seven microliters and, with particular preference, of approximately five microliters as measurement area has proved to be particularly practical. The holding area, whose diameter can be of the order of magnitude of a few millimeters up to a few centimeters, preferably has a volume of the order of magnitude of milliliters, in particular two milliliters or fewer, preferably approximately one milliliter. The result of this dimensioning is that during the examination of typical cell cultures a compressed cell cake is formed only in the measurement area, whereas after the centrifugation the holding area is filled exclusively with supernatant.

The scale transformation leads on the one hand, to the possibility of very accurately reading off the heights of the individual cell cake sections, since even small volume changes lead to comparatively large height changes in the corresponding cell cake section that can be read off effectively. On the other hand, this embodiment facilitates the determination of the staining profile or staining gradient for the purpose of ascertaining the distribution of differently damaged cells, since the optical density of the cell cake perpendicular to its height is very low. In the event of staining with a light absorbing dye such as, for example, trypan blue, very accurate staining values can be measured in transmission, particularly even in the range of strong staining.

Alternatively, it is also possible to use fluorescing or phosphorescing dyes, these being more generally expressed as light emitting dyes. In the case of this embodiment of the inventive method, use is to be made of a conventional fluorescence measurement arrangement for illumination during evaluation. The low optical density of the cell cake perpendicular to its height has the advantage here that artifacts owing to scattering or reabsorption can be very largely avoided.

It is provided in an advantageous development of the inventive method that an imaging sensor images the cell cake and transmits a digital image to a data processing device that analyzes the digital image according to prescribed rules in order to determine the heights of the cell cake sections. This permits automated evaluation. The person skilled in the art is familiar with image recognition algorithms that are able to measure in an automated way the height of the imaged cell cake, and the distribution of its staining. The term of imaging sensor is to be understood broadly in this case, and covers both a planar sensor such as, for example, a CCD sensor, and a line-array sensor suitably aligned with the cell cake, or a sensor device that scans the cell cake.

As mentioned, the fact that cells of different viability can differ in their density plays an important role in the present invention. However, on the other hand this leads to the fact that the relative heights of individual cell cake sections do not directly reproduce the relative volume distribution of the corresponding cells in the sample that is not compressed as cell cake. It is correspondingly provided in the case of a preferred embodiment of the inventive method that in order to calculate the proportions of cells of different viability, the ascertained heights of the cell cake sections are weighted with weighting parameters that represent different densities of cell material of different viability. Consequently, the influence of the different compression of the individual sections in the cell cake can be corrected. This is preferably performed automatically by the data processing device.

Relative centrifugal forces of 2000 to 3000 g, in particular at 2250 to 2750 g, in particular at approximately 2500 g have proved to be entirely feasible for carrying out the centrifugation step. Periods from 0.5 to 5 minutes, in particular 0.5 to 2 minutes, in particular approximately 1 minute have proved to be advantageous centrifugation times. A centrifugation over approximately 1 minute with relative centrifugal forces of approximately 2500 g have proved to be optimum standard values for the centrifugation step. "Optimum" signifies in this case the best possible compromise between the method efficiency, that is to say method duration, in particular, adequate compression of the cell cake, reproducibility of the result and dimensional accuracy of the result after centrifugation.

Further features and advantages of the invention emerge from the following, special description and the drawings, in which:

FIG. 1 shows a schematic of a preferred embodiment of a sample vessel;

FIG. 2 shows a view, rotated by 90° above the axis of symmetry, of a sample vessel in accordance with FIG. 1;

FIG. 3 shows an enlarged illustration of the measuring range of a sample vessel in accordance with FIG. 1;

FIG. 4 shows three sample vessels in accordance with FIG. 1, in a preferred embodiment of a sample holder;

Figure 5:
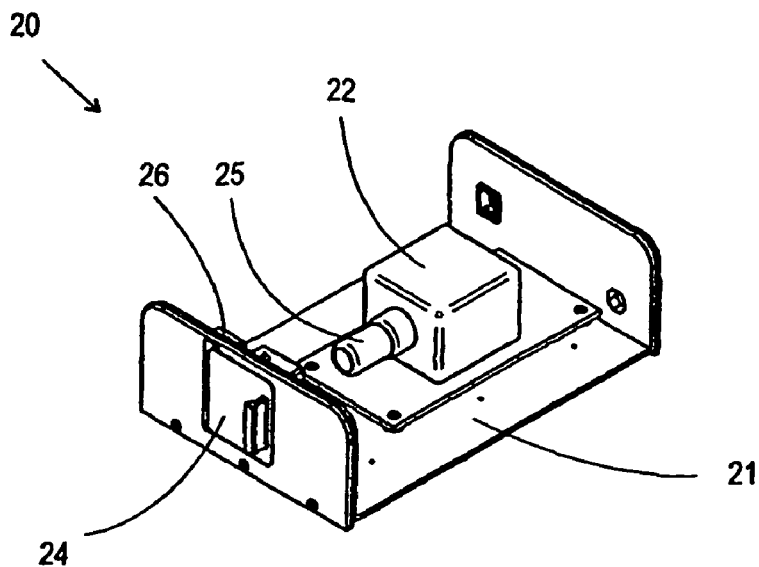
FIG. 5 shows a first perspective illustration of an embodiment of a readout unit.

FIGS. 1 and 2 show a schematic of a particularly preferred embodiment of a sample vessel, specifically a so-called PCV tube 10, for carrying out the inventive method. The PCV tube 10 can be subdivided into two main areas. A first, large-volume area I is denoted here as holding area I. A second area II, designed as a capillary, is denoted here as measuring area. In the case of the embodiment illustrated in FIGS. 1 and 2, the holding area is subdivided in to two subareas: an essentially cylindrical main area Ia, and a conically tapering transition area Ib. Typical dimensions for the holding area I are of the order of magnitude of cm, while its typical volume is of the order of magnitude of approximately 1 ml. The measuring area II is designed as a capillary with a typical inside diameter of approximately 500 µm. Its typical volume is approximately 5 µl. It may expressly be pointed out that these dimensions only represent exemplary dimensions that have proved themselves in practice. These can be adapted by the person skilled in the art in view of the particular application without departing from the core of the present invention. Particularly in cases where high PCV values are to be expected, the volume of the measuring area II can be of larger configuration. In cases where cultures of particularly large cells are to be tested, the inside diameter of the capillary of the measuring area II can, for example, be of correspondingly large configuration. The opposite holds, of course, analogously for cases of particularly small cells and/or low expected PCV values.

At least in its measuring area II, the PCV tube is produced from transparent material, preferably from transparent plastic. Two stabilizing wings 12 are provided adjoining the measuring area II and the transition area Ib in the case of the particularly advantageously embodiment illustrated in FIGS. 1 and 2. The stabilizing wings 12 are preferably designed in one piece with the outer walls of the measuring area II and of the transition area Ib, and run such that an unimpeded view on to the measuring area II is possible, at least for a given orientation of the PCV tube 10. Although two stabilizing wings 12 are illustrated in the embodiment illustrated in FIG. 1 and 2, their number is not basically restricted. Again, instead of wings 12 there could be one or more stabilizing members, for example in a cylindrical extension of the main holding area Ia.

However, the unimpeded possibility of looking in is important in at least one orientation of the PCV tube 10.

In order to carry out the inventive method, a cell suspension representative for a cell culture to be tested is stained with a viability dye. As already mentioned, trypan blue constitutes a suitable such dye. However, a person skilled in the art will know of further such dyes which stain individual cells more or less strongly depending on the viability thereof. This includes both absorbing and light emitting, in particular fluorescing or phosphorescing dyes.

After a sufficient incubation time, that is to say after the dye has had a time to act on the cell suspension that is suitable for staining the cells to be tested as a function of viability, the cell suspension is centrifuged in the PCV tube 10. A centrifugation of approximately 2500 g over approximately 1 min has proved to be particularly advantageous. Substantially weaker relative centrifugal forces and/or shorter centrifugation times lead to an inadequate compression of the cell cake. In the event of substantially larger relative centrifugal forces, by contrast, a re-expansion of the cell cake is observed after conclusion of the centrifugation step. This leads to undesired measuring inaccuracies. Substantially longer centrifugation times do not lead to any appreciable improvement in compression or reproducibility of the result and are therefore not sensible because of the attendant prolongation of the method duration. However, it may be mentioned that particular cell types require other centrifugation parameters for result optimization. The average person skilled in the art is aware of how to make an appropriate choice.

FIG. 3 shows the measuring area II of a PCV tube 10 in an enlarged, schematic illustration. A cell cake 13 has been deposited in the lower region of the capillary. The cell cake 13 is subdivided into three sections of different. height. The completely intact cell are located in a first cell cake section 131, which is deposited in the lower region of the capillary 11 because of the high density of the material forming it. Said cells are not stained in the exemplary embodiment shown, since their cell membranes have withstood a penetration of the viability dye. Dead cells and cell fragments are contained in a further region 133, which forms the uppermost region of the cell cake 13 because of the particularly low density of the material forming it. The cell membranes have not been able here to oppose a penetration of the viability dye, and so the region 133 is distinguished by maximum staining. Extending between the regions 131 and 133 is a region 132 that contains those cells whose degree of viability lies between completely intact and completely dead. As illustrated schematically in FIG. 7, a color gradient is formed in this region; it will be examined in detail later.

FIG. 4 shows an advantageous tube holder for holding one or more PCV tubes 10. The holder 14 essentially comprises a cover plate 15 with cutouts whose diameter corresponds substantially to the outside diameter of the PCV tubes 10, and a baseplate 16 on which the PCV tubes 10 stand. The cover plate 15 and the baseplate 16 are connected by separating walls 17 that in a preferred embodiment of the invention constitute an optical insulation between the individual PCV tubes. The front and rear sides of the holder preferably remain free in order to enable a flat illumination of the PCV tube, and observation of the transmission light. In the case of the embodiment illustrated, there are provided in the baseplate of the holder additional openings 18 that also permit illumination parallel to the direction in which the PCV tubes 10 extend; this is advantageous particularly in the case of the use of a fluorescence viability dye.

The holder 14 can comprise any desired number of chambers for holding PCV tubes 10. The individual chambers are preferably dimensioned such that even conventional centrifugation tubes to whose dimensions the preferred PCV tubes 10 are adapted, can be put down therein. In a particularly advantageous embodiment of the holder 14, the latter is configured such that it can be used in commercially available centrifuges. This enables a number of PCV tubes 10 to be simultaneously inserted into, or removed from a centrifuge.

Figure 6:
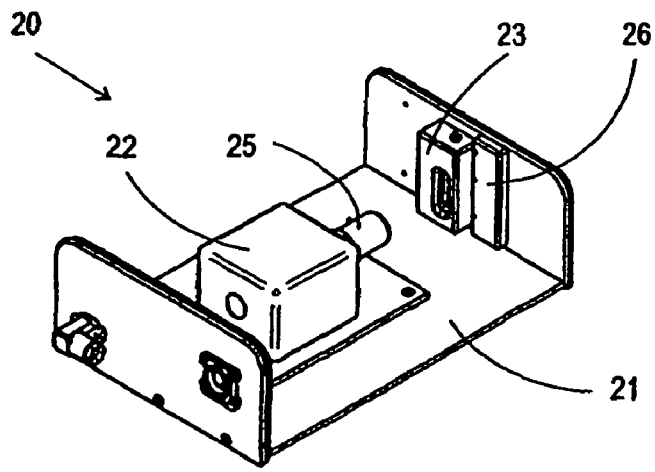
FIG. 6 shows a second perspective illustration of the readout unit according to FIG. 4.

FIGS. 5 and 6 show a preferred embodiment of a reader 20 for evaluating the measurement result ascertained with the inventive method. The reader comprises a preferably light-proof housing 21, of which only a lower support part is illustrated in FIGS. 5 and 6. A preferably provided corresponding cover is not shown in FIGS. 5 and 6. The reader 20 further comprises an imaging sensor 22 that is preferably configured as a planar CCD camera. Alternatively, it is also possible to provide line-array sensors or scanning photosensors. Furthermore, the reader 20 comprises a sample holder 23 that is preferably arranged on the inner side of a swiveling door 24 in an end face of the reader 20. The holding device 23 is preferably matched to the dimensions of the PCV tubes 10 and, for example, fashioned with use of guides and/or snap-on clips such that inserted sample vessels always exhibit the same positioning and alignment. In the case of the preferred embodiment illustrated in FIGS. 5 and 6, a sample vessel can easily be inserted into the sample holder 23 when the door 24 is open. Subsequently closing the door 24 positions the sample vessel opposite the sensor 22, and simultaneously seals the housing 21 in lightproof fashion.

An imaging optics 25 that images at least the region of the compressed cell cake 13 in the sample vessel on to the sensor 22 is provided as a function of the specific configuration of the sensor 22 and its orientation relative to the sample holder 23. In order to be imaged on to the sensor 22, the sample in the sample holder 23 is illuminated by an illumination arrangement 26 that is arranged next to the sample holder 23 in the embodiment illustrated. It is preferred to perform the illumination with an arrangement of one or more light-emitting diodes whose light is preferably coupled in to the sample holder such that the sample, in particular the measuring area II of a PCV tube 10 is uniformly irradiated from behind. Alternatively, or in addition, it is also possible to provide other options for coupling in other or further light sources. For example, external light sources such as, for example, external lasers can be coupled in via mirrors or glass fibers. The provision of various options for coupling in, in particular with the use of standard components, enables a simple and variable use of the reader 20 for different viability dyes and illumination requirements. As an alternative to the sample holder 23 illustrated, it is also possible to provide a plurality of sample holders, in particular ones that are suitable for accommodating the previously described holders 14, but being advantageous to provide a manual or motorized drive that permits an automated sample feed and an automated sample evaluation.

The sensor 22 is preferably coupled to a digital data processing device. This can be an external computer, or else a microprocessor that is arranged in the housing 21. The data processing device picks up the digital images produced by the sensor and feeds them to an evaluation process in accordance with prescribed rules. The aim of the evaluation is to determine the height of the cell cake and, in particular, of the individual cell cake sections in the sample vessel. A person skilled in the art knows of suitable image processing algorithms to this end.

Figure 7:
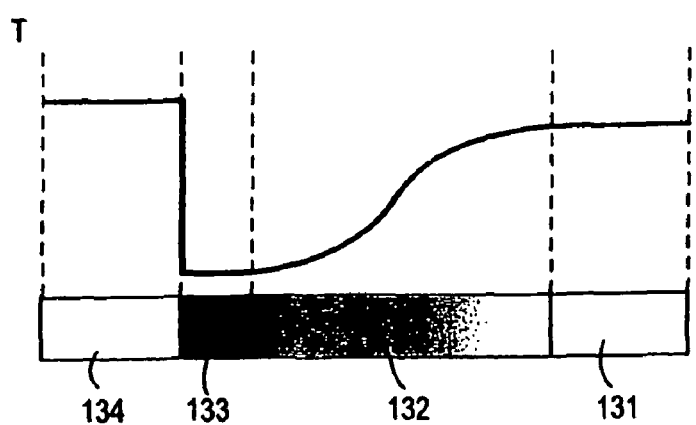
FIG. 7 shows a schematic of a result curve as result of the inventive method.

In a particularly preferred embodiment of the inventive method, the color profile in the middle cell cake section 132 is additionally analyzed in detail. A schematic curve is illustrated FIG. 7. A measuring area of a PCV tube 10 is illustrated schematically in the lower portion of FIG. 7. The different cell cake sections are clearly to be recognized, specifically their section 131 with completely intact cells, the region 133 with completely dead cells and cell fragments, and the middle region 132 with cells of different degrees of damage. Additionally to be recognized in FIG. 7 is a further region 134 which, like the region 131, is not stained. This is an "empty section" of the measuring area that is not completely filled up by the cell cake in the example shown. Supernatant, that is to say solids-free sample solution, collects in this section 134. Said sample solution is not stained.

A transmission curve such as could arise, for example, from the analysis of the illustrated measuring area, is illustrated schematically in the upper portion of FIG. 7. Since it is free from cells, section 134 exhibits a very high transmission. By contrast therewith, the section 133 exhibits maximum staining, that is to say minimum transmission. As an interface, the transition between the sections 134 and 133 is discontinuous. The transmission is substantially constant in the section 133. In section 131, which is remote, the transmission is likewise constant, but lies at a substantially higher level. In the example of FIG. 7, this level lies somewhat below the transmission level in section 134 since, because of the dense cell packing, it is necessary here to take account of light scattering, and thus of a slightly decreased transmission as against the pure supernatant in section 134. By contrast, a constant color profile results between the sections 133 and 131 in the intermediate section 132. An analysis of this region can permit a differentiated statement concerning the "state of health" of the cell culture tested that goes beyond simply a quantitative determination of the total cell volume and the volumes of dead and intact cells. A similar or analogous scheme also exists, of course, for a measurement in a reflection or emission mode. Here, the person skilled in the art will adjust the illumination appropriately to the special optical requirements of the measurement, and interpret as appropriate the image resulting as measurement result, or have it evaluated automatically by an appropriate apparatus.

Of course, the embodiments discussed in the specific description and shown in the figures constitute merely illustrative exemplary embodiments of the present invention. A broad spectrum of modification options are available to the person skilled in the art. In particular, the choice of the cells, the dyes, the shapes and dimensions of the vessels, the illumination arrangement and the readout apparatus is subject to being adjusted by the person skilled in the art to respectively particular objects and conditions of application.

The invention claimed is:

1. A method for determining the viability of cells in cell cultures, comprising the steps of:
    staining a sample of the cells by a dye that can penetrate into individual cells as a function of their viability, and determining portions of the cells stained with different intensities, characterized by centrifuging a cell suspension of the stained cells as a sample in a sample vessel (10); wherein the sample vessel (10) has a holding area (I) and a measuring area (II) that adjoins the holding area (I), the measuring area (II) defining a capillary having an inside diameter substantially smaller than an inside diameter of the holding area (I); the centrifuging being carried out until a solids content present in the sample has been deposited as a compressed cell cake (13) and determining proportions of volumes of differently stained sections (131, 132, 133) of the compressed cell cake (13) to determine the proportions of cells of different viability.

2. The method as claimed in claim 1, characterized in that determining the proportions of the volume of the differently stained sections is undertaken by measuring heights of differently stained cell cake sections (131, 132, 133).

3. The method as claimed in claim 2, characterized in that in order to determine the distribution of cells of different degree of damage, the step of measuring the heights of the differently stained sections comprises measuring the heights of the differently stained sections along a staining profile extending in a direction of the cell cake height of at least one section (132) of the cell cake (13).

4. The method as claimed in claim 3, characterized in that the step of measuring the heights of the differently stained sections comprises using an imaging sensor (22) to generate digital images of the cell cake (13) and transmitting the digital images to a data processing device that analyzes the digital images to determine the heights of the cell cake sections (131, 132, 133).

5. The method as claimed in claim 2, characterized in that the step of determining the proportions of cells of different viability comprises weighting the measured heights of the cell cake sections (131, 132, 133) in proportion to known densities of cell material of different viability.

6. The method as claimed in claim 1, characterized in that the step of staining the sample of the cells by a dye that can penetrate into individual cells as a function of their viability comprises using a dye that is a light absorbing and/or light scattering dye.

7. The method as claimed in claim 1, characterized in that the step of staining the sample of the cells by a dye that can penetrate into individual cells as a function of their viability comprises using a dye that is a light emitting dye.

8. The method as claimed in claim in claim 1, characterized in that the centrifuging step is performed with relative centrifugal forces from 2000 to 3000 g.

9. The method as claimed in claim 8, characterized in that the centrifuging step is carried out for 0.5 to 5 min.

10. A method for determining viability of cells in a culture having cells varying in viability from high density viable cells to low density dead cells, the method comprising: staining a sample of the cells by a dye that penetrates into individual cells in an amount inversely proportional to their density; centrifuging a suspension of the stained cells as a sample in a sample vessel (10); wherein the sample vessel (10) has a holding area (I) and a measuring area (II) that adjoins the holding area (I), the measuring area (II) defining a capillary having an inside diameter substantially smaller than an inside diameter of the holding area (I); the centrifuging being carried out so that centrifugal forces distribute the cells substantially in accordance with their density, the centrifuging being carried out until a solids content present in the sample has been deposited as a compressed cell cake (13) defining a staining gradient ranging from highly stained low density dead cells to minimally stained high density viable cells; and measuring heights of differently stained sections of the cell cake (13) to determine proportions of the cells of different viability.

11. The method of claim 10, wherein the measuring is carried out by generating digital images of the staining gradient in the cell cake (13), transmitting the digital images of the staining gradient to a data processing device and analyzing the digital images of the staining gradient with the data processing device to determine proportions of the cells of different viability.

12. The method of claim 10, wherein the step of staining a sample of the cells is carried out with a dye that is a light absorbing and/or light scattering dye.

13. The method of claim 10, wherein the step of staining a sample of the cells is carried out with a dye that is a light emitting dye.

* * * * *